United States Patent
Mathuis et al.

(10) Patent No.: US 12,055,540 B2
(45) Date of Patent: Aug. 6, 2024

(54) DIGITAL HOLOGRAPHIC MICROSCOPY FOR DETERMINING A VIRAL INFECTION STATUS

(71) Applicant: OVIZIO IMAGING SYSTEMS NV/SA, Brussels (BE)

(72) Inventors: Philip Mathuis, Asse (BE); Serge Jooris, Gistoux (BE)

(73) Assignee: OVIZIO IMAGING SYSTEMS NV/SA, Brussels (BE)

( * ) Notice: Subject to any disclaimer, the term of this patent is extended or adjusted under 35 U.S.C. 154(b) by 177 days.

(21) Appl. No.: 16/976,429

(22) PCT Filed: Mar. 15, 2019

(86) PCT No.: PCT/EP2019/056547
§ 371 (c)(1),
(2) Date: Aug. 27, 2020

(87) PCT Pub. No.: WO2019/175386
PCT Pub. Date: Sep. 19, 2019

(65) Prior Publication Data
US 2021/0142472 A1    May 13, 2021

Related U.S. Application Data

(60) Provisional application No. 62/643,364, filed on Mar. 15, 2018.

(30) Foreign Application Priority Data

Mar. 15, 2018   (BE) .................................. 2018/5158

(51) Int. Cl.
G06V 10/764   (2022.01)
G01N 15/14    (2006.01)
(Continued)

(52) U.S. Cl.
CPC ..... G01N 33/5026 (2013.01); G01N 15/1468 (2013.01); G01N 33/5091 (2013.01);
(Continued)

(58) Field of Classification Search
None
See application file for complete search history.

(56) References Cited

U.S. PATENT DOCUMENTS 3,701,586 A  * 10/1972 Goetz .................... G02B 26/06
                                                       348/40
2011/0317158 A1* 12/2011 Lyng ...................... G01N 21/65
                                                       356/301
(Continued)

FOREIGN PATENT DOCUMENTS

EP         1 631 788          5/2004
WO    WO 2011/049965 A1       4/2011
(Continued)

OTHER PUBLICATIONS

Altawaty et al. "Lack of LT [beta] R Increases Susceptibility of OPEC-J2 Cells to Porcine Epidemic Diarrhea Virus", Cells vol. 7, No. 11, Nov. 21, 2018 (Nov. 21, 2018), p. 222, XP055530082, figure 4.
(Continued)

*Primary Examiner* — Tsung Yin Tsai
(74) *Attorney, Agent, or Firm* — Knobbe, Martens, Olson & Bear, LLP (57) ABSTRACT

A method for providing a viral infection status of at least one cell in a cell sample comprising receiving holographic information (304) of the cell sample obtained by digital holographic microscopy, and determining from the holographic information, the viral infection status (306) of the at least one cell.

12 Claims, 4 Drawing Sheets

(51) Int. Cl.
- *G01N 33/50* (2006.01)
- *G03H 1/00* (2006.01)
- *G03H 1/04* (2006.01)
- *G06T 7/00* (2017.01)
- *G06T 7/40* (2017.01)
- *G06V 20/69* (2022.01)
- *G01N 15/10* (2006.01)
- *G01N 15/1434* (2024.01)
- *G06N 3/08* (2023.01)

(52) U.S. Cl.
CPC ......... *G03H 1/0005* (2013.01); *G03H 1/0443* (2013.01); *G06T 7/0012* (2013.01); *G06T 7/40* (2013.01); *G06V 10/764* (2022.01); *G06V 20/695* (2022.01); *G06V 20/698* (2022.01); G01N 2015/1006 (2013.01); G01N 2015/1454 (2013.01); G03H 2001/005 (2013.01); G06N 3/08 (2013.01); G06T 2207/10056 (2013.01); G06T 2207/20036 (2013.01); G06T 2207/20081 (2013.01); G06T 2207/20084 (2013.01); G06T 2207/30024 (2013.01)

(56) References Cited

U.S. PATENT DOCUMENTS

| | | | | |
|---|---|---|---|---|
| 2012/0183987 A1* | 7/2012 | Gevaert | ............ | G01N 33/5011 435/325 |
| 2012/0218379 A1* | 8/2012 | Ozcan | ............ | G03H 1/06 348/40 |
| 2012/0248292 A1* | 10/2012 | Ozcan | ............ | G03H 1/0866 250/208.1 |
| 2013/0203145 A1* | 8/2013 | Lambert | ............ | C12N 13/00 435/173.1 |
| 2013/0210066 A1* | 8/2013 | Pavillon | ............ | G03H 1/0866 435/288.7 |
| 2014/0376816 A1* | 12/2014 | Lagae | ............ | G03H 1/22 382/134 |
| 2016/0102284 A1* | 4/2016 | Lipkens | ............ | C12M 35/04 435/308.1 |
| 2017/0248512 A1* | 8/2017 | Di Carlo | ............ | G01N 15/1429 |
| 2019/0242819 A1* | 8/2019 | Frumker | ............ | H01S 3/005 |
| 2019/0250558 A1* | 8/2019 | Javidi | ............ | G01N 21/453 |
| 2021/0142472 A1* | 5/2021 | Mathuis | ............ | G01N 33/5026 |

FOREIGN PATENT DOCUMENTS

| | | |
|---|---|---|
| WO | WO 2013/010595 A1 | 1/2013 |
| WO | WO 2013/010999 A1 | 1/2013 |
| WO | WO 2013/076082 A1 | 5/2013 |
| WO | WO 2013076089 | 5/2013 |
| WO | WO 2013120886 | 8/2013 |
| WO | WO 2014044823 | 3/2014 |
| WO | WO 20170205222 | 11/2017 |

OTHER PUBLICATIONS

Hakim et al. "Analysis of quantitative phase obtained by digital holography on H&E-stained pathological samples", Artifical Life and Robotics, Springer Japan, Tokyo, vol. 24, No. 1, Sep. 18, 2018 (Sep. 18, 2018)m pp. 38-43, XP036734012.

International Search Report and Written Opinion mailed Jul. 29, 2019 in International Application No. PCT/EP2019/056547.

Jian-Hai et al "[Three-dimensional morphology of C6/36 cells infected by dengue virus: a study based on digital holographic microscopy]", Medline, US National Library of Medicine (NLM), Bethesda, MD, US, 2017, XP002787126.

Ribeiro et al "Digital holographic microscope: A new tool to follow on real time intracellular infections with obligate intracellular microorganisms and the effect of interferon", Journal of Interferon and Cytokine Research, vol. 27 No. 8, 2007, p. 737, XP055530096.

Bishop, Christopher M. "Pattern Recognition and Machine Learning" 2006, Springer Schience+Business Media, LLC, New York, NY, USA.

Gonzalez et al. "Digital Image Processing (4th Edition)" 2018, Pearson Education, Inc. Hoboken, NJ USA.

Goodfellow et al, "Deep Learning" 2016, The MIT Press.

https://en.wikipedia.org/wiki/Machine_learning.

https://en.wikipedia.org/wiki/Deep_learning.

Office Action issued in Canadian Application No. 3,091,080, dated Nov. 8, 2023.

* cited by examiner

DIGITAL HOLOGRAPHIC MICROSCOPY FOR DETERMINING A VIRAL INFECTION STATUS

CROSS REFERENCE TO RELATED APPLICATIONS

This application is the U.S. National Phase under 35 U.S.C. § 371 of International Application PCT/EP2019/056547, filed Mar. 15, 2019, designating the U.S., and published in English as WO 2019/175386 A1 on Sep. 19, 2019, which claims priority to Belgium Patent Application No. 2018/5158, filed Mar. 15, 2018, and U.S. Provisional Patent Application No. 62/643,364, filed Mar. 15, 2018. Any and all applications for which a foreign or domestic priority claim is identified here or in the Application Data Sheet as filed with the present application are hereby incorporated by reference under 37 CFR 1.57.

FIELD

The present invention relate to a method of determining a viral infection status of at least one cell in cell sample using holographic information obtained from digital holographic microscopy (DHM).

BACKGROUND

Determination of infectious viral diseases can be achieved using several different techniques.

The plaque assay technique is useful for viral quantification, where a monolayer of cells is infected with a virus causing the infected cells to lyse. Surrounding cells will then become infected and eventually a larger area of the monolayer will appear clear. The area known as plaques can be counted to measure viral infection. However, detection is slow since viral detection is only determined at the lysis stage.

Other methods include analysing the cells using a macromolecular probe such as an antibody or using a nucleic amplification technique such as PCR. Use of PCR or antibody probe requires much time and effort, while it is important for viral infections to be quickly identified. Antibodies also require identification of antigen marker on the cell membrane; hence different antibodies may be needed according to the cell type, presenting antigen, and infecting virus. The task of identifying suitable antigen markers is a time consuming process.

There is a need for a rapid, flexible method for determining a viral status of cells in a cell sample, that can be applied to a range of different cell types and infecting virus, and that dispenses with a requirement to identify protein or nucleic acid disease markers.

SUMMARY

Provided herein is a method for providing a viral infection status of at least one cell in a cell sample comprising receiving holographic information (304) of the cell sample obtained by digital holographic microscopy, and determining from the holographic information, the viral infection status (306) of the at least one cell, wherein the infection status (306) is determined from cellular parameter data (312) comprising one or more measured cellular parameters (308) of the cell derived from the holographic information wherein the one or more measured cellular parameters, MCPs, (308) comprises a subset of the MCPs of Table 1, where the subset comprises one or more MCP from at least one of the groups (a) Phase Texture (F40 to F51), (b) Refraction Peak (F20, F33-F37), (c) Morphology (F2-F19, F70-72).

The subset may comprise one or more (group (a)) MCPs selected from F45 (ID PhaseCorrelationFeature), F44 (ID PhaseContrastFeature), F48 (ID PhaseSkewnessFeature), F47 (ID PhaseHomogeneityFeature), F43 (ID PhaseAverageUniformityFeature), F51 (ID PhaseUniformityFeature).

The subset may comprise one or more (group (b)) MCPs selected from F20 (ID EquivalentPeakDiameterFeature), F33 (ID PeakAreaFeature), F34 (ID PeakAreaIlormalizedFeature), F36 (ID PeakHeightFeature), F37 (ID PeakHeightNormalizedFeature).

The subset may comprise one or more (group (c)) MCPs selected from F8 (ID EquivalentCellDiameterFeature), F17 (ID RadiusMeanFeature), F8 (ID Equivalent Diameter), F3 (ID CellAreaFeature), F18 (ID RadiusVarianceFeature), F6 (ID ElongatednessFeature), F4 (ID CircularityFeature).

The subset may further comprises one or more MCPs of group (d) Optical Height (F24-F32, F38-F39), optionally selected from F27 (ID OpticalHeightMeanFeature), F32 (ID OpticalVolumeFeature), F38 (ID OpticalHeightStandardDeviationFeature), F39 (ID OpticalHeightStandardDeviationInMicronFeature).

The subset may comprise
F45 (ID PhaseCorrelationFeature) and F44 (ID PhaseContrastFeature),
or
F45 (ID PhaseCorrelationFeature), F44 (ID PhaseContrastFeature), and F48 (ID PhaseSkewnessFeature),
or
F45 (ID PhaseCorrelationFeature), F44 (ID PhaseContrastFeature), F48 (ID PhaseSkewnessFeature), and F20 (ID EquivalentPeakDiameterFeature),
or
F45 (ID PhaseCorrelationFeature F44 (ID PhaseContrastFeature), F48 (ID PhaseSkewnessFeature), F20 (ID EquivalentPeakDiameterFeature, and F33 ((ID PeakAreaFeature or F34 (ID PeakAreaIlormalizedFeature)).

Provided herein is a method for providing a viral infection status of at least one cell in a cell sample comprising receiving holographic information (304) of the cell sample obtained by digital holographic microscopy, and determining from the holographic information, the viral infection status (306) of the at least one cell.

The infection status (306) may be determined from cellular parameter data (312) comprising one or more measured cellular parameters (308) of the cell derived from the holographic information.

The one or more measured cellular parameters (308) may comprise one or more of the parameters of Table 1.

The cellular parameter data (312) may further comprise one or more derived parameters determined from the one or more measured cellular parameters of the at least one cell, including
at least one ratio of a measured cellular parameter of a cell and another different measured cellular parameter of the same cell,
an indication of a variation between two or more cells in the cell sample of a measured cellular parameter.

The determining may comprise using a predictive model trained using a training set of cells of known viral infection status and measured cellular parameters.

The predictive model may use a machine learning method such as a neural network method, random forest trees or deep learning method.

The sample may be a static or flowing cellular suspension, or an adherent cell culture.

The viral infection status of the at least one cell includes one or more of: an indication of a presence or absence of a viral infection, a probability of an infection, a degree of infection, a stage of infection, quantity of virus.

The method may further comprise outputting a report comprising the viral infection status of the at least one cell.

The method may be performed at a remote processing centre.

Further provided herein is a system comprising:
a computing device configured to execute the method s described here, and
a digital holographic microscope, DHM.

The DHM may comprise a light source emitting at least partially coherent light, an interferometer, and an image sensor.

Further provided herein is a computing device configured to perform a method as described here, said computing device configured to:
receive holographic information of at least one cell in a cell sample obtained by digital holographic microscopy (DHM), and
determine from the holographic information, viral infection status of the at least one cell.

Further provided herein is a computer program having instructions which when executed by a computing device or system cause the computing device or system to perform the method as described herein.

Further provided herein is a computer readable medium having stored thereon the computer program.

DETAILED DESCRIPTION OF CERTAIN EMBODIMENTS

Before the present methods, systems, devices and products of the invention are described, it is to be understood that this invention is not limited to particular methods, systems, devices and products or combinations described, since such methods, systems, devices and products and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, 24 4, ≥5, ≥6, or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In the present description of the invention, reference is made to the accompanying drawings that form a part hereof, and in which are shown by way of illustration only of specific embodiments in which the invention may be practiced. Parenthesized or emboldened reference numerals affixed to respective elements merely exemplify the elements by way of example, with which it is not intended to limit the respective elements.

It is to be understood that other embodiments may be utilised and structural or logical changes may be made without departing from the scope of the present invention. The following detailed description, therefore, is not to be taken in a limiting sense, and the scope of the present invention is defined by the appended claims.

Herein is a method for providing information on viral infection status of at least one cell in a cell sample comprising receiving holographic information from said cell sample obtained by digital holographic microscopy (DHM), and determining from the holographic information, the viral infection status of the at least one cell of the cell sample.

The holographic information may be used to determine cellular parameter data comprising one or more measured cellular parameter for each cell in the sample, from which the viral infection status can be determined for each cell or cells in the sample.

The viral status may be provided in "real time". By "real-time" is a means that the status is regularly updated (e.g. 1-5 times/min) to reflect changes in virus load as cells in the sample are incubated. The sample may be a flowing suspension. The sample may be a flowing suspension pumped from and returned to a bioreactor.

The cell sample comprises one or a plurality of cells. The one or a plurality of cells may be derived from a biological organism that comprises cells from said biological organism. The biological organism may be any for instance, animal, insect, yeast, or bacterial. The one or a plurality of cells is may be derived from an animal, preferably from a mammal, e.g. from a cat, a dog, a swine, a horse, a cattle, a sheep, a goat, a rabbit, a rat, a mouse, a monkey. The one or a plurality of cells may be derived from a human being. The one or a plurality of cells in the cell sample may or may not be labelled; as mentioned elsewhere in, labelling is not necessary for holographic determination of viral status.

The cell sample may comprise a liquid suspension containing the one or a plurality of cells in a suspended state in a liquid. It is appreciated that liquid in which the cells are suspended might depend to the nature of the cell sample (e.g. body fluid, blood, excretion, bioreactor . . . ).

The cell sample may be provided as a static (non-flowing) liquid suspension in relation to the DHM image sensor. The cell sample may be provided as a flow of liquid suspension in relation to the DHM image sensor e.g. pumped from and optionally returned to a vessel. Acquiring holographic information of a flow allows the label-free and real time measurement of viral infection status. Other viral detection techniques may not be sufficiently fast or accurate for the monitoring of a sample flow; techniques that rely on macromolecular probes consume large quantities of probe, and the labelled cells cannot be returned to the vessel. The term vessel as used herein refers to a container or a canalisation system capable of holding and/or guiding a liquid wherein cells to be analysed of interest are present. As such, the term vessel includes a reactor, an incubator, container, bio-reactor, fermentation reactors, water supply piping or plumbing, water canalization systems, water purification reactors, brewing reactors, micro-reactors, etc.

The cell sample must be sufficiently transparent to allow passage of light emitted by the DHM light source. Light scattering should be sufficiently reduced in order not to significantly affect interference processes on which DHM relies. It is understood that the cell density is such that cells are not extensively overlapped e.g. light passes through the volume of observation and the incident photons on the image sensor result from an integration of all the cells in the volume.

Figure 1:
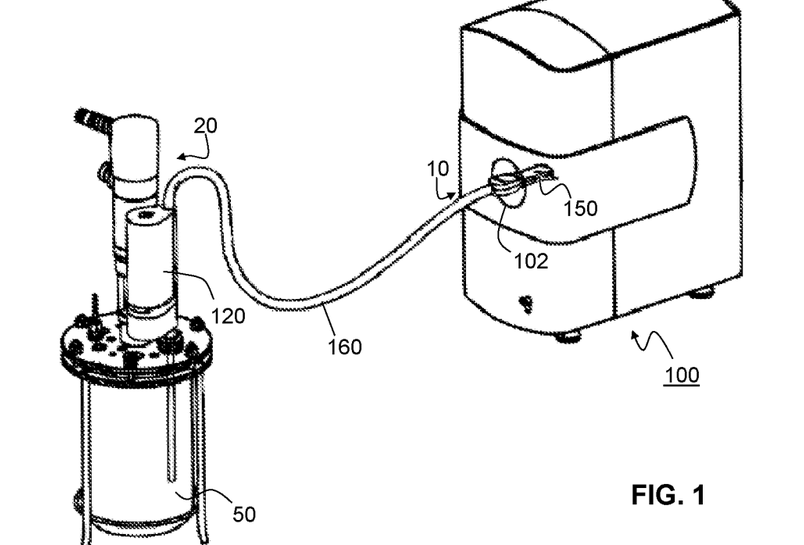
FIG. 1 depicts an arrangement of a DHM connected to a vessel that is a bio-reactor from which sample is pumped for analysis.
Figure 2:
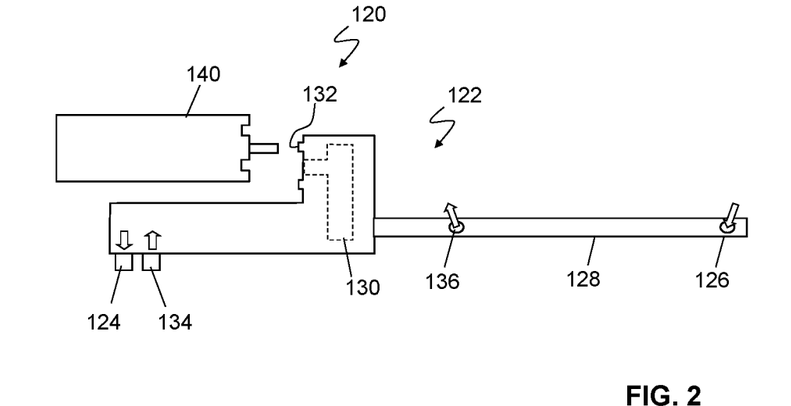
FIG. 2 depicts an arrangement of a dismountable pump assembly for a vessel.
Figure 3:
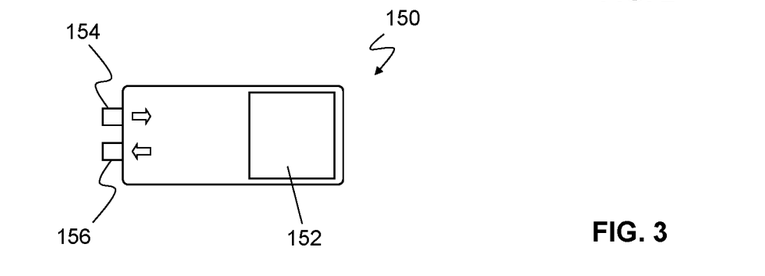
FIG. 3 illustrates a dismountable conduit for a DHM.

Exemplary elements of a DHM in combination with a flowing sample is show, for instance, in FIGS. 1 to 3. A system comprising a DHM (100), a reactor (50), DHM-dismountable conduit (also known as a cartridge) (150), connected to a dismountable pump assembly (120) by a tubing assembly (160) is shown in FIG. 1. The DHM (100) may be provided with a docking element (102) configured to receive the dismountable conduit (150) for the passage of a sample flow, which docking element (102) is configured to position a transparent part (152, FIG. 3) of the dismountable conduit in relation to the DHM image sensor and/or DHM light source for acquisition of the holographic information. The transparent part (152) is configured for the passage of light emitted by the DHM light source. The dismountable conduit (DC) (150) has a DC inlet (154) for inflow of liquid suspension, and a DC outlet (156) for its outflow.

The dismountable conduit (150) is fluidly connected or connectable to the vessel (50) using a tubing assembly (160) comprising at least one tube (160) having a proximal end (10) and a distal end (20). The terms "distal" or "distal to" and "proximal" or "proximal to" is understood to mean towards (proximal) or away (distal) from the DHM. Thus, "proximal" or "proximal to" means towards the DHM and, therefore, away from the e.g. the vessel. Conversely, "distal" or "distal to" means towards away from the DHM and away from e.g. the vessel. A proximal end of the tubing assembly (160) may be connected to the dismountable conduit (150). A distal end of the tubing assembly (160) may be connected to a dismountable pump assembly (120) configured to draw and pump fluid from the vessel (50) through the tubing assembly (160) and towards the dismountable conduit (150).

The dismountable pump assembly (120) (FIG. 2) may comprise a fluid conducting part (122) that is an arrangement of one or more conduits having a sample outlet (124) that is connected or connectable to a distal end (20) of an outflow tube of the tubing assembly (160), and a sample inlet (126) that is in contact or contactable with the vessel (50) contents. The sample inlet (126) is typically disposed on an end of a projecting element (128) comprised in the fluid conducting part (122) that separates the sample inlet (126) from the sample outlet (124) and connects them. The length of the projecting element (128) may be determined according to the size of the vessel (50) and the height of liquid therein. The fluid conducting part (122) is also disposed with a flow induction mechanism (130) that when actuated, for instance by the application of torque, induces flow of liquid from the sample inlet (126) to the sample outlet (124). The flow induction mechanism (130) may be determined according to the sample type and pressure requires; the skilled person may choose from a variety of mechanisms such as those found in a positive displacement pump or velocity pump for instance. The fluid conducting part (122) may comprise a coupling (132) for attachment to a dismountable actuator (140) for the supply of force (e.g. torque) to the flow induction mechanism. The dismountable actuator (140) may comprise an electric motor. Sample from the vessel (50) flows under induced flow from sample inlet (126) to the sample outlet (124), through the outflow tube of tubing assembly (160) connected to the DC inlet (154) of the dismountable conduit (150).

The fluid conducting part (122) may further comprise a sample return inlet (134) that is connected or connectable to a distal end (20) of a return flow tube of tubing assembly (160), and in fluid connection in the fluid conducting part (122) with a sample return outlet (136). The sample return outlet (136) may be typically disposed on the aforementioned projecting element (128) at a different position from the sample inlet (126). Sample returning from the dismountable conduit (150) (from the DC outlet (156)) flows through the return flow tube of tubing assembly (160) into the sample return inlet (134) of the fluid conducting part, through the sample return outlet (136) and into the vessel (50). The fluid conducting part (122) may be disposable. The fluid conducting part (122) is preferably formed from a rigid material. An example of a dismountable conduit, dismountable pump assembly flow system, and tubes suitable for use with a vessel and a DHM are described in WO 2014/044823 and US 2017/0205222.

The DHM-dismountable conduit (also known as a cartridge) (150), dismountable pump assembly (120) and tubing assembly (160) may be provided as a sterile disposable kit, preferably without the dismountable actuator (140).

Figure 4:
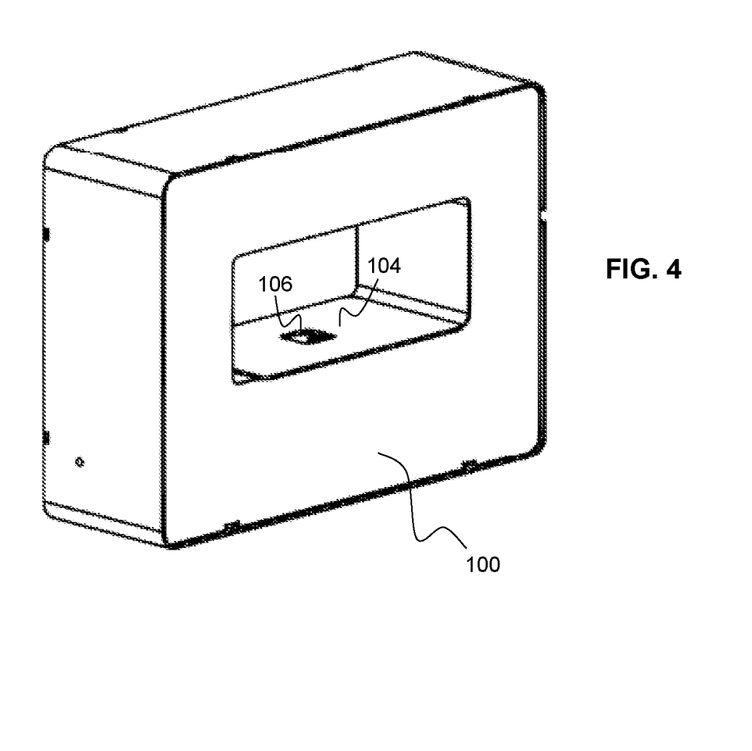
FIG. 4 shows a DHM suitable for obtaining holographic information of an adherent cell culture.

The sample may comprise cells on a support substrate, incorporated into a glass or plastic container, or microscope slide. Suitable container include multi-plate well, T-flask. The support substrate is determined such that the front focal plane of the DHM automatically falls within the cell sample, without the need of refocusing the DHM for each sample. The DHM may be provided with a sample holder configured to receive the support substrate in the requisite form (e.g. as a microscope slide or container). The sample holder may be moveable (e.g. displaceable and/or rotatable) to allow different regions of the support substrate to be acquired. In FIG. 4, an exemplary DHM (100) is depicted comprising a stationary sample holder that is a stage (104) onto which the container is placed and a window (106) for the passage of light, for instance from the sample to the image sensor or of light emitted by the light source.

The support substrate is used in adherent cell culture, wherein cells are cultured in a suitable medium and adhere to and spread over the support substrate, typically in a monolayer. Adherent cell culture is used to propagate certain animal (e.g. mammalian) cells that are anchorage dependent. The cell sample must be sufficiently transparent to allow passage of light emitted by the DHM light source. Light scattering should be sufficiently reduced in order not to significantly affect interference processes on which DHM relies. It is understood that the cell density is such that cells are not extensively overlapped e.g. light passes through the volume of observation and the incident photons on the image sensor result from an integration of all the cells in the volume.

The present method is suitable for detection of different viral infections. The virus may be a DNA virus or an RNA virus. The virus may be any, for instance but not limited to, Epstein-Barr virus, flu virus, hepatitis B virus, herpes virus, Human T lymphotrophic virus type 1 (HTLV-I), hepatitis C virus, Adenovirus, Adeno-associated virus (AAV), lentivirus or baculovirus.

Holographic information refers to information, generally being phase and amplitude information, which can be obtained through a digital holographic microscope (DHM) from the cell sample. In particular, said holographic information may include a digital hologram acquired by the DHM, an intensity image derived from the digital hologram, a quantitative phase contrast image derived from the digital hologram, or a combination of these. The intensity image and quantitative phase contrast image may be obtained from the digital hologram by hologram reconstruction.

The images—usually the quantitative phase contrast images—are then segmented in order to delineate individual cells from the background, thereby generating a plurality of segmented images from the holographic images. The process of segmentation is known in the art, for instance, from watershed treatment, clustering-based image threshold and using neural networks. Various algorithms exist for watershed treatment, including Meyers flooding algorithm and optimal spanning forest algorithms (watershed cuts). Cluster-based image thresholding may employ Otsu's method. The holographic information may include the segmented images. The measured cellular parameters are then determined for an individual cell in the image segment.

The cellular parameter data comprises:

one or more measured cellular parameters (MCP) of a cell (see Table 1 below), and/or one or more derived parameters determined from the one or more measured cellular parameters e.g. transformation of two or more MCPs of the same cell, or transformation of one or more of the same MCP for two or more different cells.

A derived parameter may include:

at least one ratio of a measured cellular parameter of a cell and another (different) measured cellular parameter of the same cell. The ratio may be any one of (F1) to (73) with any other one of (F1) to (F73) of Table 1. A ratio may be any one of (F67)-(F73) with any other of (F67)-(F73), a ratio (F68) with (F69), a ratio (F68) with (F67), a ratio any of (F68) to (F73) with (F67).

an indication of a variation between two or more cells in the cell sample of a measured cellular parameter. For instance a derived parameter—nuclear size variability—may be determined from F70 and is the standard deviation of the nuclear volumes of cells present in one or multiple fields of view. Another derived parameter—nuclear volume variability—may be derived from F71 and is the variability of the statistical distribution of all nuclear volumes analyzed.

From the cellular parameter data, information on the viral infection status of the cell in the sample may be determined. Where the cellular parameter data comprises an indication of variation (e.g. nuclear size variability, nuclear volume variability) between two or more cells in the cell sample of a measured cellular parameter, the viral infection status may regard two or more cells in the cell sample.

The holographic information may be used to determine one or more measured cellular parameters (MCP) for an individual cell in the cell sample. An MCP is a parameter that is measured for a cell or for a cellular component (e.g. nuclear size, optical height of any of the inner structure of the cell, for instance but not limited to the cytoplasm optical height, optical nuclear height) from holographic information. Table 1 lists examples (F1 to F73) of MCPs of a cell.

TABLE 1

Measured cellular parameters (MCPs) of a cell as determined from holographic information. "No." refers to the code used herein to identify the MCP, "ID" refers to the attribute name used by standard software to label the MCP, "Category" refers to the class of MCP, "Group" refers to a more refined classification of MCP, and "Description" provides measurement information.

| MCP | No. | ID | Category | Group | Description |
|---|---|---|---|---|---|
| Intensity Variance | F1 | IntensityStandardDeviationFeature | Intensity texture | Intensity texture | Variance value of the intensity over the cell surface |
| Aspect Ratio | F2 | AspectRatioFeature | Morphology | (c) Morphology | Ratio of the principal axis of the minimal surface ellipsoid |
| Surface | F3 | CellAreaFeature | Morphology | (c) Morphology | The surface of the cell |
| Circularity | F4 | CircularityFeature | Morphology | (c) Morphology | Ratio between the area of the cell to the square perimeter. The ratio is between 0 and 1, and express the fact that the cell is close to a perfect circle or not (1 = circular, 0 = not circular) |
| Compactness | F5 | CompactnessFeature | Morphology | (c) Morphology | Ratio of the area and the variance of an object in the axis for discrimination between a circular and star shaped object |
| Elongatedness | F6 | ElongatednessFeature | Morphology | (c) Morpholoqy | Aspect ratio normalised between 0 and 1 |
| Elongation | F7 | ElongationFeature | Morphology | (c) Morphology | Ratio of the width and height of the minimum enclosing rectangle |
| Diameter | F8 | EquivalentCellDiameterFeature | Morphology | (c) Morpholoqy | Diameter of the circle that has the same area as the cell |
| Hu Moment 1 | F9 | HuMoment1Feature | Morphology | (c) Morphology | Weighted average (moment 1) of the image pixels' intensities geometry |
| Hu Moment 2 | F10 | HuMoment2Feature | Morphology | (c) Morphology | Weighted average (moment 2) of the image pixels' intensities geometry |
| Hu Moment 3 | F11 | HuMoment3Feature | Morphology | (c) Morphology | Weighted average (moment 3) of the image pixels' intensities geometry |
| Hu Moment 4 | F12 | HuMoment4Feature | Morphology | (c) Morphology | Weighted average (moment 4) of the image pixels' intensities geometry |
| Hu Moment 5 | F13 | HuMoment5Feature | Morphology | (c) Morphology | Weighted average (moment 5) of the image pixels' intensities geometry |
| Hu Moment 6 | F14 | HuMoment6Feature | Morphology | (c) Morphology | Weighted average (moment 6) of the image pixels' intensities geometry |
| Hu Moment 7 | F15 | HuMoment7Feature | Morphology | (c) Morphology | Weighted average (moment 7) of the image pixels' intensities geometry |
| Perimeter | F16 | PerimeterFeature | Morphology | (c) Morpholoqy | Perimeter of the cell. |
| Radius Mean | F17 | RadiusMeanFeature | Morphology | (c) Morphology | The mean of the cell radius. The cell radius is measured by taking successively all the points belonging to the perimeter of the cell and measuring the distance to the centre of mass of the cell |
| Radius Variance | F18 | RadiusVarianceFeature | Morphology | (c) Morphology | The standard deviation of the cell radius. The cell radius is measured by taking successively all the points belonging to the perimeter of the cell and measuring the distance to the center of mass of the cell |
| Normalized Radius Variance | F19 | RadiusVarianceNormalizedFeature | Morphology | (c) Morphology | Radius Variance/Equivalent Cell Diameter |
| Refraction Peak Diameter | F20 | EquivalentPeakDiameterFeature | Optical | (b) Refraction Peak | The diameter of the circle that has the same area as the refractive peak |
| Maximum Intensity: | F21 | IntensityMaximumFeature | Optical | Intensity | Maximum value of the intensity over the cell surface |
| Intensity | F22 | IntensityMeanFeature | Optical | Intensity | Average value of the intensity over the cell surface |

TABLE 1-continued

Measured cellular parameters (MCPs) of a cell as determined from holographic information. "No." refers to the code used herein to identify the MCP, "ID" refers to the attribute name used by standard software to label the MCP, "Category" refers to the class of MCP, "Group" refers to a more refined classification of MCP, and "Description" provides measurement information.

| MCP | No. | ID | Category | Group | Description |
|---|---|---|---|---|---|
| Minimum Intensity | F23 | IntensityMinimumFeature | Optical | Intensity | Minimum value of the intensity over the cell surface |
| Mass excentricity | F24 | OpticalHeightCentroidDistanceFeature | Optical | (d) Optical Height | Distance in pixels between the geometric centre the cell and the centre of mass of the cell ponderated by the optical height |
| Optical Height Maximum | F25 | OpticalHeightMaximumFeature | Optical | (d) Optical Height | Maximum value of optical height over the cell surface in radian |
| Optical Height Maximum (μm) | F26 | OpticalHeightMaximumInMicronFeature | Optical | (d) Optical Height | Maximum value of optical height over the cell surface in microns |
| Optical Height | F27 | OpticalHeightMeanFeature | Optical | (d) Optical Height | Average value of optical height over the cell surface (in radian) |
| Optical Height Mean (μm) | F28 | OpticalHeightMeanInMicronFeature | Optical | (d) Optical Height | Average value of optical height over the cell surface (in microns) |
| Normalized Optical Height | F29 | OpticalHeightMeanNormalizedFeature | Optical | (d) Optical Height | Optical Height In Micron/ Equivalent Cell Diameter |
| Optical Height Minimum | F30 | OpticalHeightMinimumFeature | Optical | (d) Optical Height | Minimum value of optical height over the cell surface in radian |
| Optical Height Minimum (μm) | F31 | OpticalHeightMinimumInMicronFeature | Optical | (d) Optical Height | Minimum value of optical height over the cell surface in microns |
| Optical Volume | F32 | OpticalVolumeFeature | Optical | (d) Optical Height | Optical volume of the cell. The optical volume is proportional to the volume of the cell and to its refractive index. The optical volume is to the volume what the optical height is to the height. |
| Refraction Peak Surface | F33 | PeakAreaFeature | Optical | (b) Refraction Peak | The area of the refractive peak in microns. If there are several refractive peaks, the sum of all peaks area |
| Normalized Peak Area | F34 | PeakAreaNormalizedFeature | Optical | (b) Refraction Peak | Peak Area/(Cell Area * Intensity Mean * Intensity Mean) |
| Aggregate size | F35 | PeakCountFeature | Optical | (b) Refraction Peak | The number of refractive peaks in the cell. The value is 1 for an isolated cell, N for an aggregate of N cells |
| Refraction Peak Intensity | F36 | PeakHeightFeature | Optical | (b) Refraction Peak | The maximum intensity of the refractive peak |
| Normalized Peak Height | F37 | PeakHeightNormalizedFeature | Optical | (b) Refraction Peak | Peak Height/(Surface * Intensity Mean) |
| Optical Height Variance | F38 | OpticalHeightStandardDeviationFeature | Phase texture | (d) Optical Height | Variance of the optical height over the cell surface in radians |
| Optical Height Variance (μm) | F39 | OpticalHeightStandardDeviationInMicronFeature | Phase texture | (d) Optical Height | Variance of the optical height over the cell surface in microns |
| Phase Average Contrast | F40 | PhaseAverageContrastFeature | Phase texture | (a) Phase texture | Average measure of intensity contrast of the phase image |
| Phase Average Entropy | F41 | PhaseAverageEntropyFeature | Phase texture | (a) Phase texture | Measures the randomness of the element of G[1], |
| Phase Average | F42 | PhaseAveragePhaseFeature | Phase texture | (a) Phase texture | Average of the phase value over the cell surface. |
| Phase Average Uniformity | F43 | PhaseAverageUniformityFeature | Phase texture | (a) Phase texture | Average measure of uniformity of the phase over the cell surface |
| Phase Contrast | F44 | PhaseContrastFeature | Phase texture | (a) Phase texture | A measure of intensity contrast of the phase image |

TABLE 1-continued

Measured cellular parameters (MCPs) of a cell as determined from holographic information. "No." refers to the code used herein to identify the MCP, "ID" refers to the attribute name used by standard software to label the MCP, "Category" refers to the class of MCP, "Group" refers to a more refined classification of MCP, and "Description" provides measurement information.

| MCP | No. | ID | Category | Group | Description |
|---|---|---|---|---|---|
| Phase Correlation | F45 | PhaseCorrelationFeature | Phase texture | (a) Phase texture | between a pixel and its neighbour over the cell surface. A measure of how correlated a pixel is to its neighbour over the cell surface. Range: −1 to 1, corresponding to perfect positive and perfect negative correlation |
| Phase Entropy | F46 | PhaseEntropyFeature | Phase texture | (a) Phase texture | Measure the randomness of the element of G. |
| Phase Homogeneity | F47 | PhaseHomogeneityFeature | Phase texture | (a) Phase texture | Measure the spatial closeness of the distribution of G to the diagonal. Range: 0 to 1, with the maximum being achieved when the co-occurrence matrix is diagonal |
| Phase Skewness | F48 | PhaseSkewnessFeature | Phase texture | (a) Phase texture | Measure the asymmetric characteristic of the local histogram of the phase image. |
| Phase Smoothness | F50 | PhaseSmoothnessFeature | Phase texture | (a) Phase texture | A measure of the smoothness in an image, by the measure the weighted average absolute distance d of the matrix G entries from the diagonal of the matrix |
| Phase Uniformity | F51 | PhaseUniformityFeature | Phase texture | (a) Phase texture | A measure of uniformity of the phase over the cell surface, in the range 0-1. Uniformity is 1 for constant image. |
| Intensity Average Contrast | F52 | IntensityAverageContrastFeature | Intensity texture | Intensity texture | Average measure of intensity contrast of the image |
| Intensity Average Entropy | F53 | IntensityAverageEntropyFeature | Intensity texture | Intensity texture | Measures the randomness of the element of G |
| Intensity Average | F54 | IntensityAverageIntensityFeature | Intensity texture | Intensity texture | Average intensity value over the cell surface |
| Intensity Average Uniformity | F55 | IntensityAverageUniformityFeature | Intensity texture | Intensity texture | Average measure of uniformity of the intensity over the cell surface |
| Intensity Contrast | F56 | IntensityContrastFeature | Intensity texture | Intensity texture | A measure of intensity of the contrast of the intensity image between a pixel and its neighbour over the cell surface |
| Intensity Correlation | F57 | IntensityCorrelationFeature | Intensity texture | Intensity texture | A measure of how correlated the intensity of a pixel is to its neighbour over the cell surface. Range: −1 to 1, corresponding to perfect positive and perfect negative correlation |
| Intensity Entropy | F58 | IntensityEntropyFeature | Intensity texture | Intensity texture | Measures the randomness of the element of G |
| Intensity Homogeneity | F59 | IntensityHomogeneityFeature | Intensity texture | Intensity texture | Measures the spatial closeness of the distribution of G to the diagonal. Range: 0 to 1, with the maximum being achieved when the co-occurrence matrix is diagonal |
| Intensity Uniformity | F60 | IntensityUniformityFeature | Intensity texture | Intensity texture | A measure of uniformity of the intensity over the cell surface, in the range 0-1. Uniformity is 1 for constant image. |
| Intensity Skewness | F61 | IntensitySkewnessFeature | Intensity texture | Intensity texture | Measures the asymmetric characteristic of the local histogram of the intensity image. |
| Intensity Smoothness | F62 | IntensitySmoothnessFeature | Intensity texture | Intensity texture | A measure of the smoothness in an image, by |

TABLE 1-continued

Measured cellular parameters (MCPs) of a cell as determined from holographic information. "No." refers to the code used herein to identify the MCP, "ID" refers to the attribute name used by standard software to label the MCP, "Category" refers to the class of MCP, "Group" refers to a more refined classification of MCP, and "Description" provides measurement information.

| MCP | No. | ID | Category | Group | Description |
|---|---|---|---|---|---|
| | | | | | the measure the weighted average absolute distance d of the matrix G entries from the diagonal of the matrix |
| Fluorescence Maximum | F63 | FluorescenceMaximumFeature | Fluorescence (Qmod Only) | Fluorescence (Qmod Only) | Maximum value of the fluorescence intensity over the cell surface (in fluorescence arbitrary units) |
| Fluorescence Mean | F64 | FluorescenceMeanFeature | Fluorescence (Qmod Only) | Fluorescence (Qmod Only) | Average value of the fluorescence intensity over the cell surface (in fluorescence arbitrary units) |
| Fluorescence Minimum | F65 | FluorescenceMinimumFeature | Fluorescence (Qmod Only) | Fluorescence (Qmod Only) | Minimum value of the fluorescence intensity over the cell surface (in fluorescence arbitrary units) |
| Fluorescence Standard Deviation | F66 | FluorescenceStandardDeviationFeature | Fluorescence (Qmod Only) | Fluorescence (Qmod Only) | Standard Deviation value of the fluorescence intensity over the cell surface (in fluorescence arbitrary units) |
| Optical height of the nucleoli | F67 | OpticalHeightNucleoliFeature | Optical | Optical | A distance proportional to the time it takes for light to cross the nucleoli in the direction of the height and depends on both the physical height as the optical properties of the nucleoli, in particular its, possibly averaged, refraction index. |
| Optical nuclear height | F68 | OpticalHeightNucleusFeature | Optical | Optical | A distance proportional to the time it takes for light to cross the nucleus in the direction of the height and depends on both the physical height as the optical properties of the nucleus, in particular its, possibly averaged, refraction index. |
| Optical height of cytoplasm | F69 | OpticalHeightCytoplasmFeature | Optical | Optical | A distance proportional to the time it takes for light to cross the cytoplasm in the direction of the height and depends on both the physical height as the optical properties of the cytoplasm, in particular its, possibly averaged, refraction index. |
| Nuclear size | F70 | NuclearSizeFeature | Morphology | (c) Morphology | The surface area of the cell nucleus and the form that said cell nucleus adopts, being typically circular or elliptical. |
| Nuclear volume | F71 | NuclearVolumeFeature | Morphology | (c) Morphology | The numerical integration of the nuclear height over its projection in the sensor plane |
| Cell size | F72 | CellSizeFeature | Morphology | (c) Morphology | Physical dimensions of the cell, mainly the surface area of the cell |
| Chromatin texture | F73 | ChromatinTextureFeature | Intensity texture | Intensity texture | Granulometric characteristics of the chromatin in the nucleus |

Whenever absolute numbers are used to denote the optical heights, the proportionality constant is the speed of light in vacuum, unless the context dictates otherwise. Furthermore, unless explicitly stated otherwise, an optical height is expressed in this document with reference to the optical height of the liquid medium, in which case it is proportional to the difference of the time it takes for light to cross the structure (e.g. cytoplasm, nucleus, nucleolus) in the direction of the height and the time it takes for light to cross the same distance in the liquid medium. In general, one can define an optical height as the result obtained by multiplying the refractive index multiplied with the actual physical height.

The MCP may typically be a property of a whole cell (e.g. surface, circularity) or of a component of a cell (e.g. nuclear size, optical height of any of the inner structure of the cell, for instance but not limited to the cytoplasm optical height, optical nuclear height). Where in the MCP is a property of a cellular component, an image of the component of the cell isolated first, then the MCP determined on that isolated image. The skilled person knows how to process holographic images to arrive at a MCP for instance using principles of image processing as set out, for instance, in Digital Image Processing (4th Edition) by Rafael C. Gonzalez and Richard E. Woods (ISBN-13: 978-0133356724), and using a library of programming functions such as Open CV (Open Source Computer Vision).

One or more, or all of the MCPs of Table 1 may be used to determine the viral infection status. A subset of the MCPs of Table 1 may be used to determine the viral infection status. The machine learning algorithm may determine the subset of the MCPs depending on cell type and on the infecting virus.

As shown in Table 1, the MCPs may be classified into different groups such as intensity texture, morphology, refraction peak, intensity, optical height, refraction peak, phase texture, intensity texture, fluorescence, optical.

The group Phase Texture (F40-F51) contains MCPs that are a measure of variation of optical density or phase shift within the cell. The phase of light passing through a cell varies according to the local density within the cell. Regions of more density within the cell have a larger phase shift.

The group Refraction Peak (F20, F33-F37) contains MCPs that are a measure of light refracted by a cell. In particular, light refracted by a cell emerges as a conical beam; refraction peak concerns geometric characteristics of this beam.

The group Morphology (F2-F19, F70-72) contains MCPs that are a measure of a geometric property of a cell (e.g. radius, diameter etc).

The group Optical Height (F24-F32, F38-F39) contains MCPs that are a measure of thickness of an objection, in direction of the incident light.

The subset of MCPs may comprise one or more of the MCPs in at least one of the groups (a) Phase Texture (F40 to F51), (b) Refraction Peak (F20, F33-F37), (c) Morphology (F2-F19, F70-72), (d) Optical Height (F24-F32, F38-F39).

The subset of MCPs may comprise one or more of the MCPs in at least one of the groups (a) Phase Texture (F40 to F51), (b) Refraction Peak (F20, F33-F37), (c) Morphology (F2-F19, F70-72).

The subset of MCPs may comprise one or more of the MCPs in at least one of the groups (a) Phase Texture (F40 to F51), (b) Refraction Peak (F20, F33-F37), (c) Morphology (F2-F19, F70-72), and further comprise one or more MCPs of group (d) Optical Height (F24-F32, F38-F39), optionally selected from F27 (ID OpticalHeightMeanFeature), F32 (ID OpticalVolumeFeature), F38 (ID OpticalHeightStandardDeviationFeature), F39 (ID OpticalHeightStandardDeviationlnMicronFeature).

The subset of MCPs may comprise one or more of the MCPs of at least (a) Phase Texture (F40 to F51) and (b) Refraction Peak (F20, F33-F37).

The subset of MCPs may comprise one or more of the MCPs of at least (a) Phase Texture (F40 to F51).

The MCPs of groups (a) to (d) may be as set in Table 1, or be contain at least the MCP as set out in the following sections.

The subset of MCPs may comprise one or more of the MCPs in group (a) Phase Texture (F40 to F51).

The subset of MCPs may comprise one or more of the MCPs in group (a) Phase Texture selected from F45 (ID PhaseCorrelationFeature), F44 (ID PhaseContrastFeature), F48 (ID PhaseSkewnessFeature), F47 (ID PhaseHomogeneityFeature), F43 (ID PhaseAverageUniformityFeature), and F51 (ID PhaseUniformityFeature).

The subset of MCPs may comprise F45 (ID PhaseCorrelationFeature).

The subset of MCPs may comprise F45 (ID PhaseCorrelationFeature) and F44 (ID PhaseContrastFeature).

The subset of MCPs may comprise F45 (ID PhaseCorrelationFeature) and F44 (ID PhaseContrastFeature) and F48 (ID PhaseSkewnessFeature).

The subset of MCPs may comprise all of MCPs F45 (ID Phase Correlation), F44 (ID PhaseContrastFeature), F48 (ID PhaseSkewnessFeature), F47 (ID PhaseHomogeneityFeature), F43 (ID PhaseAverageUniformityFeature), and F51 (ID PhaseUniformityFeature).

The subset of MCP may comprise one or more of the MCPs in group (b) Refraction Peak (F20, F33-F37).

The subset of MCP may comprise one or more of the MCPs in group (b) Refraction Peak selected from F20 (ID EquivalentPeakDiameterFeature), F33 (ID PeakAreaFeature), F34 (ID PeakAreallormalizedFeature), F36 (ID PeakHeightFeature), and F37 (ID PeakHeightNormalizedFeature).

It is noted that F33 (ID PeakAreaFeature) and F34 (ID PeakAreallormalizedFeature) are related, and one or the other may be used. It is noted that F36 (ID PeakHeightFeature) or F37 (ID PeakHeightNormalizedFeature) are related, and one or the other may be used.

The subset of MCPs may comprise F20 (ID EquivalentPeakDiameterFeature).

The subset of MCPs may comprise all of MCPs F20 (ID EquivalentPeakDiameterFeature), either F33 (ID PeakAreaFeature) or F34 (ID PeakAreallormalizedFeature), either F36 (ID PeakHeightFeature) or F37 (ID PeakHeightNormalizedFeature).

The subset of MCP may comprise one or more of the MCPs in group (c) Morphology (F2-F19, F70-72).

The subset of MCP may comprise one or more of the MCPs in group (c) Morphology selected from F8 (ID EquivalentCellDiameterFeature), F17 (ID RadiusMeanFeature), F8 (ID Equivalent Diameter) or F3 (ID CellAreaFeature), F18 (ID RadiusVarianceFeature), F6 (ID ElongatednessFeature), and F4 (ID CircularityFeature).

It is noted that F8 (ID EquivalentCellDiameterFeature) and F17 (ID RadiusMeanFeature) are related, and one or the other may be used. It is noted that F8 (ID EquivalentCellDiameterFeature) and F3 (ID CellAreaFeature) are related, and one or the other may be used. It is noted that F18 (ID RadiusVarianceFeature) or F6 (ID ElongatednessFeature) are related, and one or the other may be used.

The subset of MCPs may comprise F8 (ID EquivalentCellDiameterFeature) or F17 (ID RadiusMeanFeature).

The subset of MCPs may comprise F8 (ID EquivalentCellDiameterFeature) or F17 (ID RadiusMeanFeature) or F3 (ID CellAreaFeature).

The subset of MCPs may comprise F8 (ID EquivalentCellDiameterFeature) or F17 (ID RadiusMeanFeature) or F3 (ID CellAreaFeature)) and (F18 (ID RadiusVarianceFeature) or F6 (ID ElongatednessFeature)) and F4 (ID CircularityFeature).

The subset of MCP may comprise one or more of the MCPs in group (d) Optical Height (F24-F32, F38-F39).

The subset of MCP may comprise one or more of the MCPs in group (d) Optical Height selected from F27 (ID OpticalHeightMeanFeature), F32 (ID OpticalVolumeFeature), F38 (ID OpticalHeightStandardDeviationFeature), and F39 (ID OpticalHeightStandardDeviationlnMicronFeature).

It is noted that F27 (ID OpticalHeightMeanFeature) and F32 (ID OpticalVolumeFeature) are related, and one or the other may be used. It is noted that F38 (ID OpticalHeightStandardDeviationFeature) and F39 (ID OpticalHeightStandardDeviationInMicronFeature) are related, and one or the other may be used.

The subset of MCPs may comprise F27 (ID OpticalHeightMeanFeature) or F32 (ID OpticalVolumeFeature).

The subset of MCPs may comprise (F27 (ID OpticalHeightMeanFeature) or F32 (ID OpticalVolumeFeature)) and (F38 (ID OpticalHeightStandardDeviationFeature) or F39 (ID OpticalHeightStandardDeviationInMicronFeature)).

The subset of MCPs may comprise F45 (ID PhaseCorrelationFeature).

The subset of MCPs may comprise F45 (ID PhaseCorrelationFeature) and F44 (ID PhaseContrastFeature).

The subset of MCPs may comprise 2 or more, preferably all of F45 (ID PhaseCorrelationFeature), F44 (ID PhaseContrastFeature), and F48 (ID PhaseSkewnessFeature).

The subset of MCPs may comprise 3 or more, preferably all of F45 (ID PhaseCorrelationFeature), F44 (ID PhaseContrastFeature), F48 (PhaseSkewnessFeature), and F20 (ID EquivalentPeakDiameterFeature).

The subset of MCPs may comprise 4 or more, preferably all of F45 (ID PhaseCorrelationFeature), F44 (ID PhaseContrastFeature), F48 (ID PhaseSkewnessFeature), F20 (ID EquivalentPeakDiameterFeature), and F33 ((ID PeakAreaFeature) or F34 (ID PeakAreaIlormalizedFeature)).

The subset of MCPs may comprise 2, 3, 4, 5 or more, preferably all of F45 (ID PhaseCorrelationFeature), F44 (ID PhaseContrastFeature), F48 (ID PhaseSkewnessFeature), F20 (ID EquivalentPeakDiameterFeature), (F33 (ID PeakAreaFeature) or F34 (ID PeakAreaIlormalizedFeature)), (F36 (ID PeakHeightFeature) or F37 (ID PeakHeightNormalizedFeature)), F47 (ID PhaseHomogeneityFeature), (F17 (ID RadiusMeanFeature) or F8 (ID Equivalent Diameter)), (F3 (ID CellAreaFeature) or F8 (ID Equivalent Diameter)), F43 (ID PhaseAverageUniformityFeature), (F32 (ID OpticalVolumeFeature) or F27 (ID OpticalHeightMeanFeature)), (F18 (ID RadiusVarianceFeature) or F6 (ID ElongatednessFeature)), F4 (ID CircularityFeature), F27 (ID OpticalHeightMeanFeature), (F38 (ID OpticalHeightStandardDeviationFeature) or F39 (ID OpticalHeightStandardDeviationInMicronFeature)), F51 (ID PhaseUniformityFeature).

Each MCP may have an equal weighting or a weight factor may be applied to one or more the measured cellular parameters, depending on the cell type and on the infecting virus. The machine learning algorithm may determine the weighting.

Digital Holographic Microscopy (DHM) is a technique which allows a recording of three dimensional information of a sample or object without the need of scanning the sample layer-by-layer. In this respect DHM is a superior technique to confocal microscopy in terms of acquisition speed. In DHM, a holographic representation is recorded by an image sensor such a CCD or CMOS. The holographic representation may be subsequently be stored or processed on a computer.

To make a holographic representation, or hologram, traditionally a light source that is coherent is used to illuminate the sample. The light source may be provided by a laser. In the most basic set-up, the light form the source is split into two beams, an object beam and a reference beam. The object beam is sent via an optical system to the sample and interacts with it, thereby altering the phase and amplitude of the light depending on the object's optical properties and 3D shape. The object beam which has been reflected on or transmitted through the sample, is then made (e.g. by set of mirrors and/or beam splitters) to interfere with the reference beam, resulting in an interference pattern which is digitally recorded. Since the hologram is more accurate when object beam and reference beam have comparable amplitude, an absorptive element can be introduced in the reference beam which decreases its amplitude to the level of the object beam, but does not alter the phase of the reference beam or at most changes the phase globally, i.e. not dependent on where and how the reference beam passes through the absorptive element. The recorded interference pattern contains information on the phase and amplitude changes which depend on the object's optical properties and 3D shape.

An alternative way of making a hologram is by using the in-line holographic technique. In-line DHM is similar to the more traditional DHM, but does not split the beam, at least not by a beam splitter or other external optical element. In-line DHM is most preferably used to look at a not-too-dense solution of particles, e.g. cells, in a fluid. Thereby some part of the at least partially coherent light will pass through the sample without interacting with the particles (reference beam) and interfere with light that has interacted with the particles (object beam), giving rise to an interference pattern which is recorded digitally and processed. In-line DHM is used in transmission mode, it needs light with a relatively large coherence length, and cannot be used if the samples are too thick or dense.

Another DHM technique called differential DHM (DDHM) is disclosed in European patent EP 1 631 788. DDHM is different to the other techniques in that it does not make use of reference and object beams in the traditional sense. In a preferred set-up of DDHM, the sample is illuminated by a light source that outputs at least partially coherent light for use in a reflection or in a transmission mode. The reflected or transmitted sample beam can be sent through an objective lens and subsequently split in two by a beam splitter and sent along different paths in a differential interferometer, e.g. of the Michelson or Mach-Zehnder type. In one of the paths, a beam-bending element or tilting mechanism is inserted, e.g. a transparent wedge or a diffraction grating. The two beams are then made to interfere with each other in the focal plane of a focusing lens and the interference pattern in this focal plane is recorded digitally by an image sensor such a CCD or CMOS. The interference pattern may be stored on a digital storage medium. Hereby, due to the beam-bending element, the two beams are slightly shifted in a controlled way and the interference pattern depends on the amount of shifting. Then the beam-bending element is turned, thereby altering the amount of shifting. The new interference pattern is also recorded. This can be done a number N of times, and from these N interference patterns, the gradient (or spatial derivative) of the phase in the focal plane of the focusing lens can be approximately computed. This is called the phase-stepping method, but other methods of obtaining the phase gradient are also known, such as a Fourier transform data processing technique. The gradient of the phase can be integrated to give the phase as a function of position. The amplitude of the light as a function of position can be computed from the possibly but not necessarily weighted average of the amplitudes of the N recorded interference patterns. Since phase and amplitude are thus known, the same information is obtained as in a direct holographic method (using a reference and an object beam), and a subsequent 3D reconstruction of the object can be performed.

The light source may emit spatially and temporally partially coherent light. The light source may emit highly correlated laser light. Spatially and temporally partially coherent light may be produced by for instance a light-emitting diode (LED). A LED is cheaper than a laser and produces light with a spectrum centred around a known wavelength, which is spatially and temporally partially coherent, i.e. not as coherent as laser light, but still coherent enough to produce holographic images of the quality which is necessary for the applications at hand. LEDs also have the advantage of being available for many different wavelengths and are very small in size and easy to use or replace if necessary. Therefore, providing a method and system which can use spatially and temporally partially coherent light for obtaining holographic images will lead to more cost-effective devices for implementing such a method.

The use of DHM in a diagnostic setting has many advantages which makes it the ideal technique to implement in a setting such as in the current invention. Besides a bright field image, a phase shift image is also created. The phase shift image is unique for DHM and gives quantifiable information about optical distance. In reflection DHM, the phase shift image forms a topography image of the object.

An object image is calculated at a given focal distance. However, as the recorded hologram contains all the necessary object wave front information, it is possible to calculate the object at any focal plane by changing the focal distance parameter in the reconstruction algorithm. In fact, the hologram contains all the information needed to calculate a complete image stack. In a DHM system, where the object wave front is recorded from multiple angles, it is possible to fully characterize the optical characteristics of the object and create tomography images of the object.

The needed components for a DHM system are inexpensive optics and semiconductor components, such as a laser diode and an image sensor. The low component cost in combination with the auto focusing capabilities of DHM, make it possible to manufacture DHM systems for a very low cost. Nevertheless, the cost of a DHM may still be too high for monitoring a large amount of reactors. For this, the present invention provides a system comprising one DHM and a set of electro-fluidic circuits which are capable of guiding fluid samples from multiple reactors to the DHM and preferably back. Hereby, only one DHM is needed to monitor multiple reactors and the overall cost can be reduced.

Generally, a DHM comprises a light source that emits coherent light or at least partially coherent light such as a LASER or LED, an interferometer which may comprise a set of mirrors and/or beam splitters, and an image sensor such as a CCD or CMOS, and a processor and a computer-readable storage medium (e.g. solid state drive, flash card, or magnetic recording device). A DHM may also comprise further optical components such as one or more lenses, mirrors, prisms, attenuators, etc. A DHM may comprise or may be connected to processing means such as a mainframe, a PC, a logical device such as a PLC, etc. A DHM may work in transmission and/or reflection mode, depending on the nature of the sample which is to be observed. A DHM may be a traditional DHM, an in-line DHM, a differential DHM, or another kind of DHM.

Figure 5:
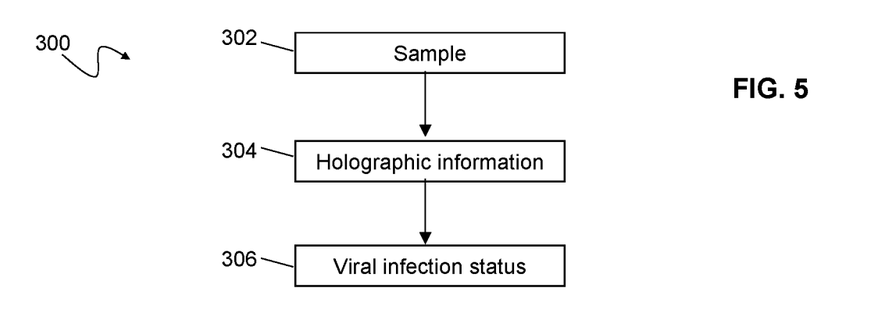
FIGS. 5 and 6 are flow charts illustrating different aspects of the method of the invention.
Figure 6:
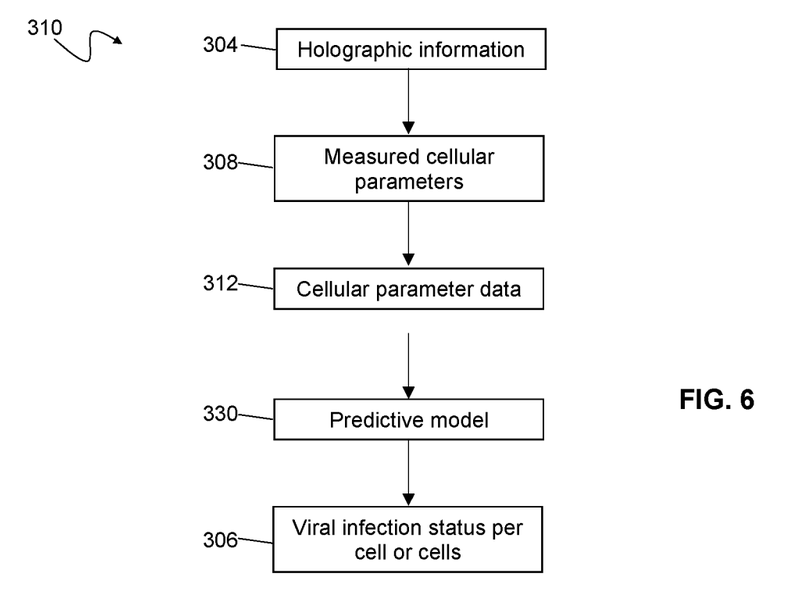

The present method (300) uses holographic information (304) of a cell sample (302) to determine viral infection status (306) as shown in FIG. 5. A pattern in the cellular parameter data is identified that correlates to a viral infection. In particular, the method may use a predictive mathematical model (330) of cellular viral infection, wherein an input to the predictive model comprises the cellular parameter data (212) derived from measured cellular parameters (308) for each cell obtained from holographic information of the cell sample (304) and the output is viral infection status (306) as exemplified in the scheme (310) of FIG. 6.

Figure 7:
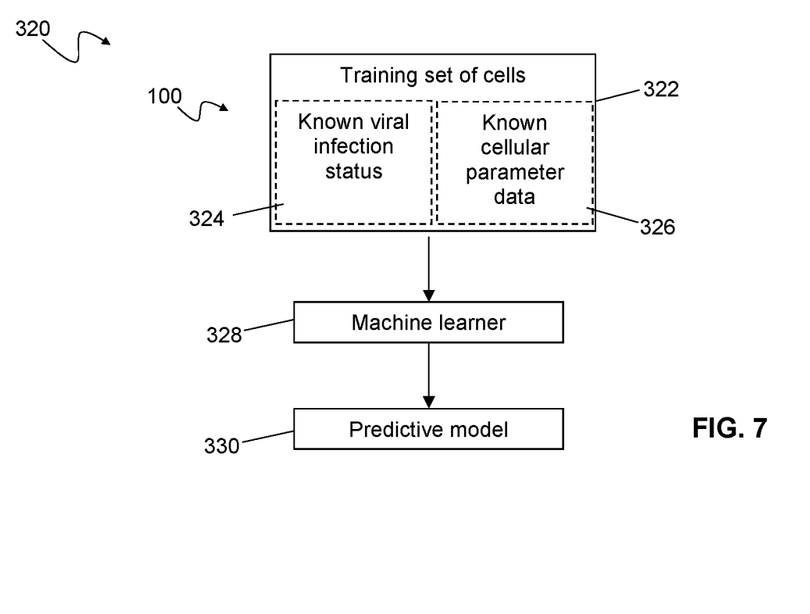
FIG. 7 flow charts illustrating a machine learning protocol.

The predictive model (330) may be created using a machine learning (328) method (e.g. neural network or random forest trees, deep learning) that is trained using a training set of cells (322), wherein the viral infection status (324) and the cellular parameter data (326) is known for each cell or cells as exemplified in the scheme (320) of FIG. 7. The viral infection status may be determined using, for instance, an antibody optionally labelled, or using a nucleic acid amplification technique such as PCR. Creation of a predictive model using machine learning (e.g. neural network or random forest trees, deep learning) is known in the art for instance from en.wikipedia.org/wiki/Machine_learning, and has also been described various publications including, for instance Pattern Recognition and Machine Learning, 2006, Christopher M. Bishop, Springer. Deep learning is known in the art, for instance, from en.wikipedia.org/wiki/Deep_learning, a do has been described in various publications, for instance, Deep Learning, 2016, Ian Goodfellow, Yoshua Bengio and Aaron Courville.

As guidance, steps for creating a simple model are described. A training set of cells comprises virally-infected cells and non-virally infected cells. The measured cellular parameters for individual cells in the training set of cell measured by DHM is obtained. The cellular parameter data, comprising the measured cellular parameter and optionally the derived parameters are provided to the learning algorithm. The machine learning method learns how to discriminate between a virally-infected cell and a non-virally infected cell based on the holographic information, in particular on the cellular parameter data, thereby creating the predictive model. The machine learning method may be supervised or unsupervised. A confusion matrix allows an error rate to be determined.

The viral infection status of the at least one cell in the sample may include an indication of a presence of an infection (yes/no), a probability of an infection (fraction), a degree of infection, a stage of infection, apoptotic state, capsid content. The viral infection status may indicate the type of virus. The viral infection status of at least 2 cells in the sample may be determining by statistically processing viral infection statuses for a plurality of cells in the sample.

The method may include a step of providing the cell sample.

The method may include a step of outputting or providing a report on the viral infection status of the at least one cell.

Further provided is a computing device configured for performing the method as described herein.

The computing device may comprise circuitry configured for performing the method of the invention. Typically the circuitry comprises a computer processor and a memory. The computing device may be implemented in one or multiple connected computers, as a cloud computing device, or other device containing the aforementioned circuitry.

The computing device may receive input data comprising one or more of:
  holographic information of the cell sample, which may include one or more of:
    a digital hologram acquired by the DHM,
    an intensity image derived from the digital hologram, a quantitative phase contrast image derived from the digital hologram,
a plurality of segmented images derived from the quantitative phase contrast image and/or the intensity image,
cellular parameter data comprising:
one or more measured cellular parameters of a cell, and/or
one or more derived parameters derived from the one or more measured cellular parameters of a cell or cells.

The input data may be electronically received e.g. over the Internet or sent via a data storage medium. The computing device might be at a location distant from the DHM, for instance in another facility, town, city, country etc.

The computing device may be configured to:
receive holographic information of at least one cell in a cell sample obtained by digital holographic microscopy (DHM), and
determine from the holographic information, viral infection status of the at least one cell The computing device may be further configured to:
output the viral infection status of the at least one cell.

The computing device may be further configured to determine from the holographic information, cellular parameter data comprising one or more measured parameters of a cell in the cell sample, from which the viral infection status of the at least one cell is determined.

The computing device may be further configured to input into the predictive model the cellular parameter data, and output from the predictive model the viral infection status of the at least one cell.

Further provided is a computer program or computer program product having instructions which when executed by a computing device or system cause the computing device or system to perform the method as described herein Further provided is a computer readable medium having stored thereon the computer program or computer program product.

Further provided is a data stream which is representative of the computer program or computer program product A remote processing centre may receive input data comprising one or more of:
holographic information of the cell sample, which may include one or more of:
a digital hologram acquired by the DHM,
an intensity image derived from the digital hologram,
a quantitative phase contrast image derived from the digital hologram,
a plurality of segmented images derived from the quantitative phase contrast image and/or the intensity image,
cellular parameter data comprising:
one or more measured cellular parameters of a cell (see below), and/or
at least one ratio of a measured cellular parameters of a cell and another (different) measured cellular parameter, and/or
an indication of a variation between two or more cells in the cell sample of a measured cellular parameter.

The input data may be electronically received e.g. over the Internet or sent via a data storage medium. The remote processing centre might be at a location distant from the DHM, for instance in another facility, town, city, country etc. The remote processing centre typically comprises a computer having a processor and memory, for instance, a server. The remote processing centre might be implemented as a cloud-based computing facility. The remote processing centre may store the input data. The remote processing centre may process the input data, in particular may execute the determining step. The remote processing centre may have access to the predictive model. The remote processing centre may send output data comprising information on viral infection status of the cell or of the sample. The output data may comprise a report containing information on viral infection status of the cell and/or of the sample.

A system may be provided comprising the computing device as described herein. The system may further comprise a DHM. The DHM may be a DHM as described herein. The DHM comprises a light source emitting at least partially coherent light, an interferometer, and an image sensor. The DHM may be provided with a docking element (102) as described herein configured to receive the dismountable conduit for the passage of a sample flow.

Example 1

Samples of SF9 cells infected with Baculovirus. Holographic data of each sample was collected at different time points after exposure to the virus. Holographic data was analysed to segregate the cells, each cell or cluster registering as an event. The segregated cells were analysed to obtained measured cellular parameters (MCPs) of individual cells or clusters. For each cell in each of samples, the MCPs according to Table 1 were obtained.

Filtering was applied to improve the quality of data set according to the following criteria of MCP: cell diameter >15 (retain)—remove debris/small cells; cell diameter <30 (retain)—remove clusters; peak height >3 (retain)—retain only cells with good viability; best depth feature <5 (retain)—keep only cells in focus.

For machine learning, 75% of the filtered data was applied to machine learning algorithms to train a classifier to obtain a random forest tree (RFT). A total of 20 trees with a depth of 10 were used. Using the trained algorithm on the remaining 25% of the filtered data, the rate of falsely predicted infected cells was found to be low and the rate of true predicted healthy cells was found to be high. The RFT ranked the discriminatory power of each measured cellular parameter according to Table 2.

TABLE 2

Ranking of discriminatory power of top 20 MCPs of Example 2.

| Rank | Discrimination power | MCP | No | ID |
|---|---|---|---|---|
| 1 | 0.190911 | Phase Correlation | F45 | PhaseCorrelationFeature |
| 2 | 0.089689 | Phase Contrast | F44 | PhaseContrastFeature |
| 3 | 0.088731 | Phase Skewness | F48 | PhaseSkewnessFeature |

TABLE 2-continued

Ranking of discriminatory power of top 20 MCPs of Example 2.

| Rank | Discrimination power | MCP | No | ID |
|---|---|---|---|---|
| 4 | 0.061248 | Refraction Peak Diameter | F20 | EquivalentPeakDiameterFeature |
| 5 | 0.054376 | Refraction Peak Surface or Normalized Peak Area | F33/F34 | PeakAreaFeature or PeakAreaNormalizedFeature |
| 6 | 0.049298 | Refraction Peak Intensity or Normalized Peak Height | F36/F37 | PeakHeightFeature or PeakHeightNormalizedFeature |
| 7 | 0.049181 | Phase Homogeneity | F47 | PhaseHomogeneityFeature |
| 8 | 0.036616 | Radius Mean or Diameter | F17/F8 | RadiusMeanFeature or Equivalent Diameter |
| 10 | 0.031089 | Surface or Diameter | F3/F8 | CellAreaFeature or Equivalent Diameter |
| 11 | 0.029854 | Phase Average Uniformity | F43 | PhaseAverageUniformityFeature |
| 12 | 0.028632 | Optical Volume or Optical Height | F32/F27 | OpticalVolumeFeature or Optical Height |
| 15 | 0.019415 | Radius Variance or Elongatedness | F18/F6 | RadiusVarianceFeature or Elongatedness |
| 17 | 0.015764 | Circularity | F4 | CircularityFeature |
| 18 | 0.013016 | Optical Height | F27 | OpticalHeiqhtMeanFeature |
| 19 | 0.012753 | Optical Height Variance (rad) or Optical Height Variance (pm) | F38/F39 | OpticalHeightStandardDeviationFeature or OpticalHeightStandardDeviationInMicronFeature |
| 20 | 0.012611 | Phase Uniformity | F51 | PhaseUniformityFeature |

Example 2

Figure 8:
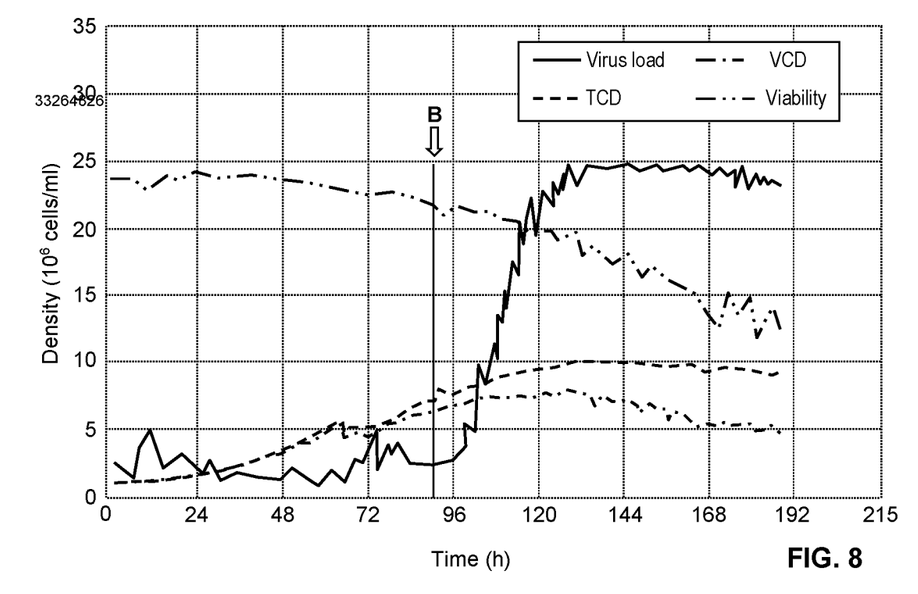
FIG. 8 is a graph of showing virus load, TCD, VCD and cell viability of Batch 1 cells in a bioreactor.
Figure 9:
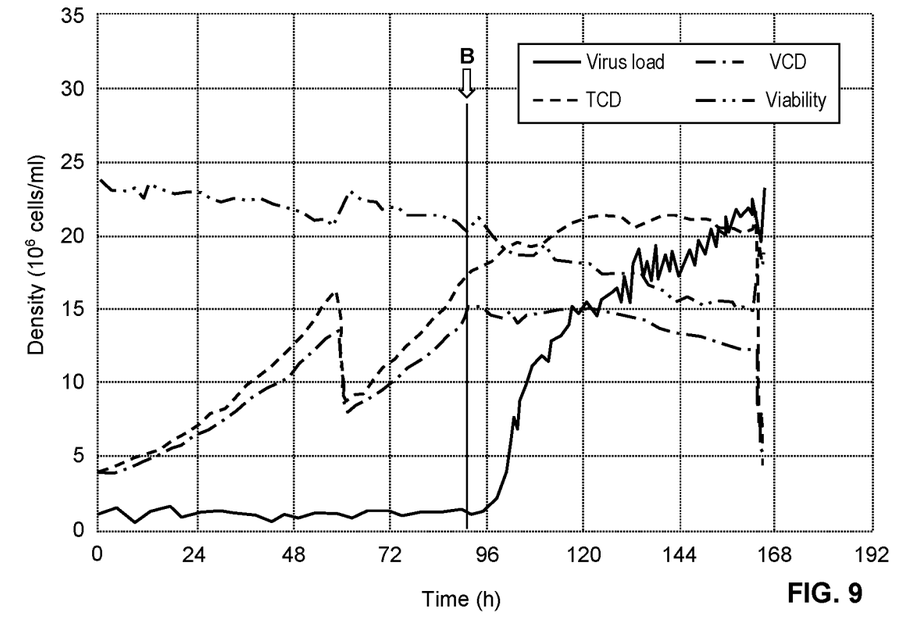
FIG. 9 is a graph of showing virus load, TCD, VCD and cell viability of Batch 2 cells in a bioreactor.

The method of the invention was used to monitor virus load of cells in flowing suspension from a bioreactor in real time. Two different batches of SF9 cells were grown in a bioreactor in liquid medium. The virus load of the cells was monitored using a method of the invention by pumping the suspension cells from the bioreactor through a flow cell having a transparent part for the passage of light for obtaining real-time images by DHM. The cells were returned to the bioreactor. Simultaneously monitored were total cell density (TCD), viable cell density (VCD), and viability. At ~90 hours (arrow B), an aliquot of Baculovirus virus was introduced into the bioreactor. The method of the invention detected an exponential increase in virus load (see FIGS. 8 (Batch 1) and 9 (Batch 2)).

What is claimed is:

1. A method for providing a viral infection status of cells incubating in a bioreactor, comprising:
   receiving holographic information of a cell sample comprising a suspension of cells from the bioreactor, and
   determining from the holographic information, the viral infection status of the cells, wherein
   the holographic information comprises an intensity image and a quantitative phase contrast image reconstructed from a digital hologram obtained by digital holographic microscopy,
   the viral infection status is determined from cellular parameter data comprising one or more measured cellular parameters (MCPs), each MCP being a value,
   the one or more MCPs are measured from the holographic information, and include at least F44 and/or F47,
   F44 is a phase texture type property measuring a contrast of the reconstructed quantitative phase image between a pixel and its neighbours over a cell surface,
   F47 is a phase texture type property measuring a spatial closeness of a co-occurrence matrix to a diagonal matrix in the reconstructed quantitative phase image.

2. The method according to claim 1, wherein the determining comprises using a predictive model trained using a training set of cells of known viral infection status and measured cellular parameters.

3. The method according to claim 2, wherein the predictive model uses a machine learning method such as a neural network method, random forest trees or deep learning method.

4. The method according to claim 1, wherein the viral infection status is provided in real time.

5. The method according to claim 1, wherein the viral infection status of the at least one cell includes one or more of: an indication of a presence or absence of a viral infection, a probability of an infection, a degree of infection, a stage of infection, quantity of virus.

6. The method according to claim 1, further comprising outputting a report comprising the viral infection status of the at least one cell.

7. The method according to claim 1 performed at a remote processing centre.

8. The method according to claim 1, wherein the suspension of cells is pumped from a bioreactor, and returned to the bioreactor after the holographic information has been obtained.

9. A system comprising:
- a computing device configured to execute the method according to claim 1, and
- a digital holographic microscope (DHM).

10. The system according to claim 9, wherein the DHM comprises a light source emitting at least partially coherent light, an interferometer, and an image sensor.

11. A computing device configured to perform a method according claim 1, said computing device configured to:
- receive holographic information of at least one cell in a cell sample obtained by digital holographic microscopy (DHM), and
- determine from the holographic information, viral infection status of the at least one cell.

12. A non-transitory computer readable medium having a program stored thereon for executing a computing device or system to carry out the method according to claim 1.

* * * * *